United States Patent [19]

Masuda et al.

[11] Patent Number: 4,494,532

[45] Date of Patent: Jan. 22, 1985

[54] TILTING HEALTH TABLE APPARATUS

[75] Inventors: Teruo Masuda, Tokyo; Kazuyuki Yamaguchi, Sayama, both of Japan

[73] Assignee: France Bed Co., Ltd., Tokyo, Japan

[21] Appl. No.: 498,142

[22] Filed: May 25, 1983

[30] Foreign Application Priority Data

Jun. 17, 1982 [JP] Japan ............................ 57-90511[U]
Dec. 10, 1982 [JP] Japan ................................ 57-216367
Feb. 17, 1983 [JP] Japan ............................ 58-21973[U]

[51] Int. Cl.[3] ................................................ A61F 5/00
[52] U.S. Cl. ...................................... 128/71; 272/144
[58] Field of Search ...................... 128/69, 71, 72, 73, 128/74; 272/144, 145; 269/323-326

[56] References Cited

U.S. PATENT DOCUMENTS 1,693,810 12/1928 Daniels et al. .
1,904,039 4/1933 Bruder ................................. 128/69
2,820,454 1/1958 Wright ............................. 128/69 X
3,286,708 11/1966 Gartner ................................ 128/71
3,568,669 3/1971 Stites .
3,589,358 6/1971 Megal .
3,815,586 6/1974 Kazik .................................. 128/69
4,232,662 11/1980 Barber ................................. 128/71

*Primary Examiner*—John D. Yasko
*Attorney, Agent, or Firm*—Frishauf, Holtz, Goodman & Woodward

[57] ABSTRACT

In a tilting health table apparatus, a pair of first handles are horizontally set on both sides of the upper end portion of a leg assembly. A table is swingably fitted to the leg assembly to securely hold the user and the table is securely set in a prescribed position by means of first, second and third stopper mechanisms. A foot board is mounted on one end portion of the table, and a pair of second handles are fitted to both sides of the foot board.

10 Claims, 15 Drawing Figures

FIG. 6
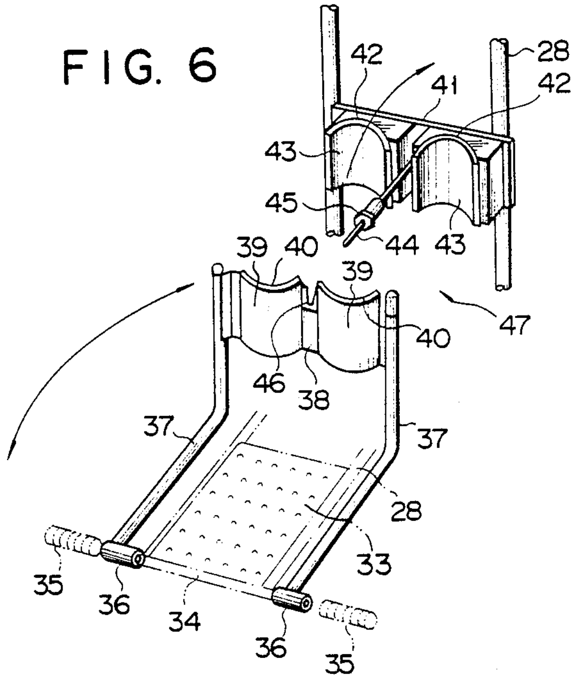
FIG. 8
FIG. 7
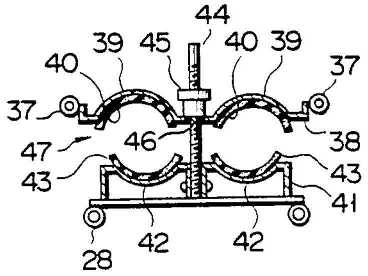
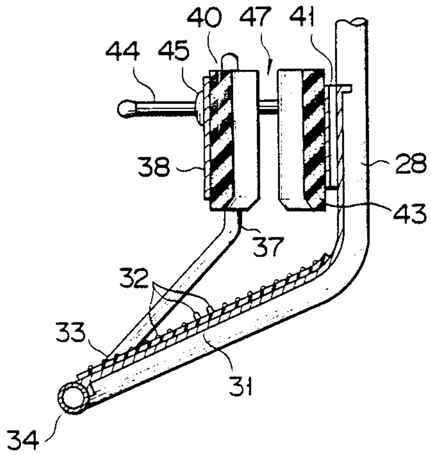

TILTING HEALTH TABLE APPARATUS

BACKGROUND OF THE INVENTION

This invention relates to a health apparatus enabling the user to perform various physical exercises.

In recent years, a great deal of attention has been drawn to physical fitness, and various kinds of exercise apparatus have been marketed. However, many of these products have only permitted the user to perform a very limited number of physical exercises. Therefore, a user desiring to perform a variety of physical exercises has been forced to purchase a number of different kinds of health apparatus, which is both inconvenient and costly.

SUMMARY OF THE INVENTION

It is accordingly the object of this invention to provide an exercise apparatus which allows the user to perform various kinds of physical exercises.

In order to achieve the above object of the present invention, there is provided a tilting health table apparatus which comprises: a leg assembly; a pair of first handles fitted in a substantially horizontal manner to both sides of the upper portion of the leg assembly; a table rotatably mounted on said leg assembly to support the user; stopper means for keeping the table in a prescribed position to restrict its movement; a foot board mounted on one end of the table; and a pair of second handles projectively fitted to both sides of said foot board.

BRIEF DESCRIPTION OF THE DRAWINGS

FIG. 6 is an exploded oblique view of a support assembly of a table;

FIG. 7 is a cross sectional view of the support assembly;

FIG. 8 is a longitudinal sectional view of the support assembly;

DETAILED DESCRIPTION OF THE PREFERRED EMBODIMENTS

Figure 2:
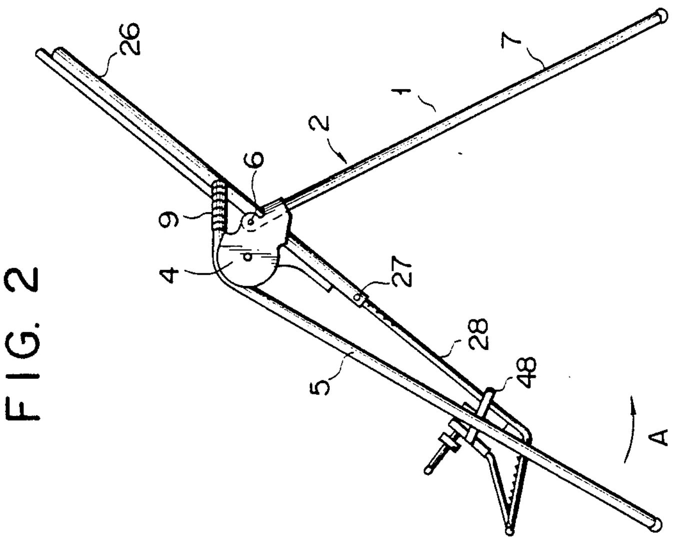
FIG. 2 is a side view thereof.
Figure 1:
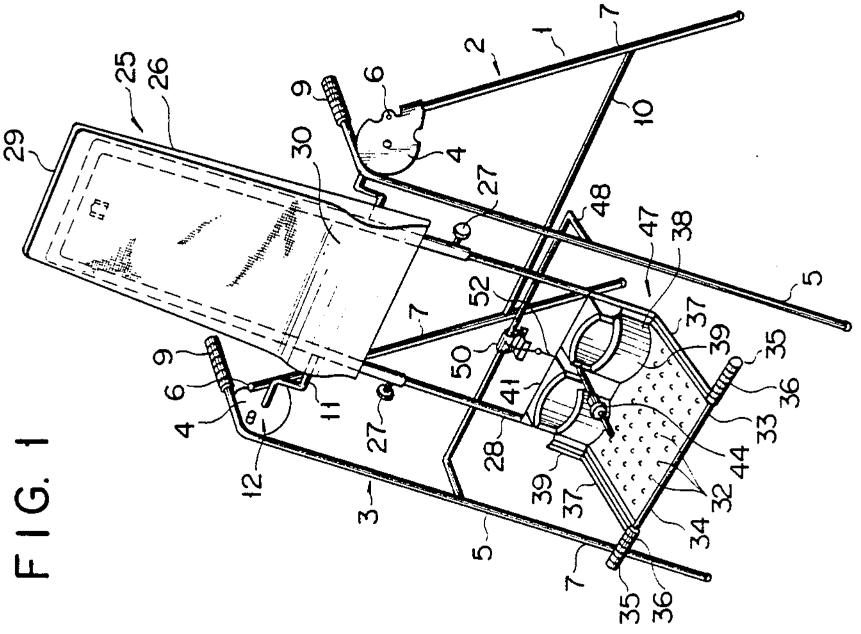
FIG. 1 is a schematic oblique view of an exercise health apparatus according to a first embodiment of the invention.
Figure 3:
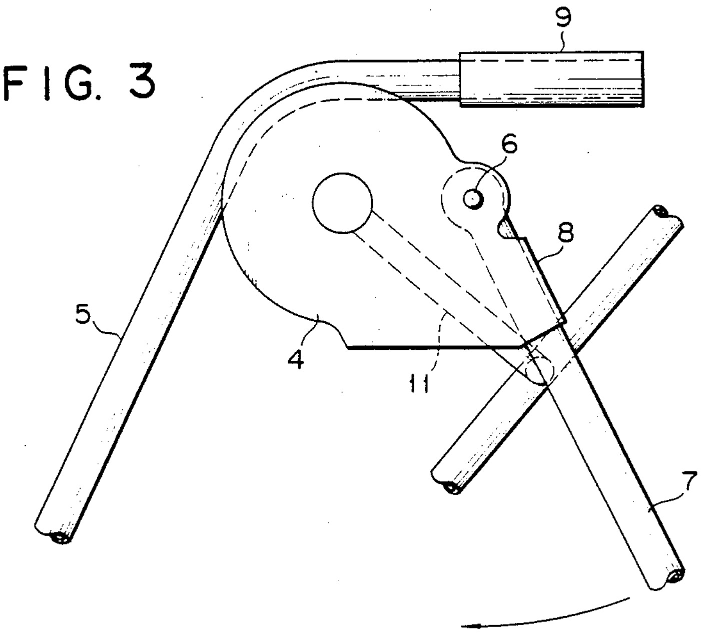
FIG. 3 is a side view of the upper portion of the leg member shown in FIG. 1.
Figure 4:
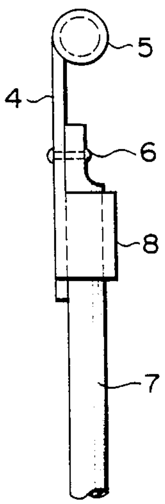
FIG. 4 is a front view of said upper portion of the leg member shown in FIG. 1.

An exercise apparatus of FIGS. 1 and 2 according to a first embodiment of this invention is provided with a leg assembly 1. This leg assembly 1 is formed of a right leg pair 2 and left leg pair 3. Each of the leg pairs 2, 3 has a fitting board 4, which in turn is provided with a fixed leg 5, whose upper end portion is securely connected to said fitting board 4, and a movable leg 7 whose upper end portion is swingably connected to said fitting board 4 by means of a pivotal shaft 6. Part of the fitting board 4 is folded to provide a stopper section 8 which restricts the movement of the movable leg 7 as shown in FIGS. 3 and 4. The upper end portion of the fixed leg 5 extends in a substantially horizontal manner. The end of said fixed leg member 5 is inserted into a first handle 9.

The movable legs 7 of the right leg pair 2 and left leg pair 3 are coupled by a connecting rod 10. A crank-shaped fitting rod 11 is rotatably set between the fitting boards 4. This fitting rod 11 is prevented from rotating by a first stopper mechanism 12. Said fitting rod 11 is formed of a pipe. The larger diameter section **13*a* of a nut 13 is engaged with both end portions of said pipe type fitting rod 11. The smaller diameter section 13*b* of the nut 13 is rotatably inserted into a support hole 14 provided in the fitting board 4. A screw 16 is threadedly fitted to the nut 13, with a washer 15 having a larger diameter than the support hole 14 set between said screw 16 and nut 13. This screw 16 prevents the smaller diameter section 13*b* of the nut 13 from falling off through the support hole 14. A base board 17 is provided at one end of the fitting rod 11 in a state facing the fitting board 4. The base board 17 is provided with a penetrating hole 18. A short pipe 19 is concentrically arranged with the penetrating hole 18 communicates and is fitted to the base board 17. A spring 22 and a stopper pin 21, whose intermediate part is provided with a flange 20, are received in the short pipe 19. The spring 22 urges the flange 20 to cause one end of the stopper pin 21 to project through the penetrating hole 18. The other end of the stopper pin 21 is provided with a knob 23. The stopper pin 21 projecting through the penetrating hole 18 is inserted into an engagement hole 24 bored in the fitting board 4, thereby restricting the extent to which the rotatable fitting rod 11 can be moved. In other words, the stopper pin 21 and engagement hole 24 jointly constitute the previously described first stopper mechanism 12 which renders the fitting rod 11** immovable in a prescribed position.

Figure 9:
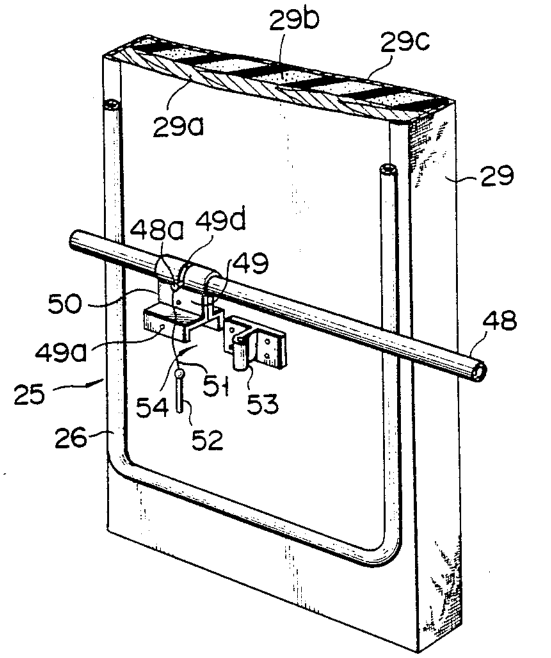
FIG. 9 is an oblique view of a third stopper mechanism.

A support member or a table 25 is fixed to the fitting rod 11 as shown in FIG. 1. As seen from FIGS. 1 and 2, the table 25 is assembled by a first substantially U-shaped pipe frame, both lateral sides of which are fixed to the fitting rod 11, and a second substantially U-shaped pipe frame 28. Both lateral portions of the second pipe frame 28 are slidably inserted into those of the first pipe frame 22. The second pipe frame 28 is normally fixed by a stop screw 27 mounted on both lateral portions of the first pipe frame 22. A cushion 29 is stretched substantially over the first pipe frame 26. A projection 30 is integrally formed with the lower end portion of the cushion 29, extending in the crosswise direction of said cushion 29. As shown in FIG. 9, the cushion 29 is fabricated by superposing an elastic member **29*b* on a base board 29*a*, and covering the elastic member 29*b* with an outer fitting 29*c*. The lower end portion of the second substantially U-shaped pipe frame 28 is bent in a front direction to form a substantially L shape as shown in FIG. 8. Between the lower end portion of the pipe frame 28, a foot board 31 is set in which the user of the subject health table apparatus puts his feet. A rubber mat 33 provided with a large number of projections 32 is placed on the surface of the foot board 31 as shown in FIG. 8. As indicated in FIG. 6, a crosswise-extending rod 34** longer than the width of the second pipe frame 28 is securely fixed to the front ends of the L-shape bent portion of the second pipe frame 28. Both end portions of a crosswise-extending rod 34 are inserted into the corresponding short pipes 36 and are projected from the short pipes 36. A second handle 35 is fitted to both end portions of said crosswise-extending rod 34. The short pipes 36 are fixed to ends of a pair of substantially L-shaped bent fitting rods 37. A first support board 38 is stretched between the L-shape bent fitting rods 37. The first support board 38 is provided with a pair of first curved sections 39 integrally formed with the first support board 38. Cushions 40 are stretched over the inner surface of each of said first curved sections 39 respectively. A second support board 41 is stretched on the lower end portions of the second pipe frame 28. The second support board 41 is provided with a pair of second curved sections 42 integrally formed with the second support board 41. The second paired curved sections 42 are arranged to face the paired curved sections 39 of the first support board 38. Cushions 43 are stretched over the inner surfaces of said second paired curved sections 42 respectively. A bolt 44 is pivotally inserted at one end between the second paired curved sections 42 of the second support board 41 as shown in FIG. 7. A nut 45 is threadedly engaged with said bolt 44. An engagement groove 46 is formed between the first paired curved sections 39 of said first support board 38 to receive the bolt 44.

When the first support board 38 is made to face the second support board 41, with the bolt 44 inserted into the engagement groove 46, and later the first support board 38 is fixed to the second support board 41 by tightening the nut 45, the legs of the user are securely held between the corresponding ones of the first paired curved sections 39 and second paired curved sections 42. In other words, the first and second support boards 38, 41 jointly constitute a support assembly 47 for firmly gripping the user's legs. The projection 30 integrally formed with the cushion 29 touches the user's waist, and keeps the user's back straight when he leans against the cushion 29.

Figure 5:
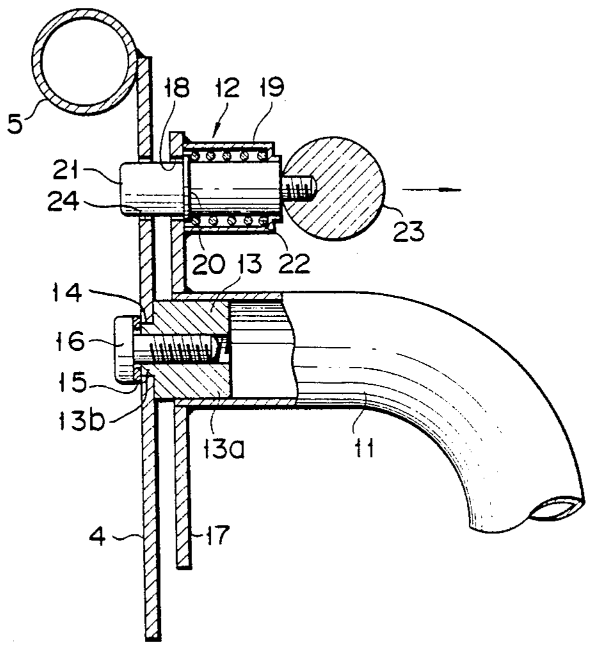
FIG. 5 is a sectional view of a first stopper mechanism.
Figure 14:
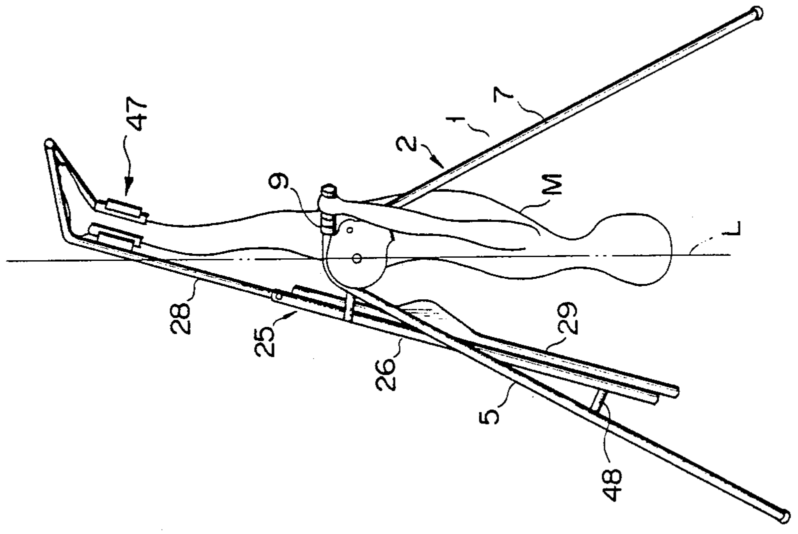

As shown in FIG. 1, a rod 48 is stretched between the paired fixed legs 5 of the leg assembly 1 to act as a second stopper mechanism designed to restrict the rotation of the table 25 projecting toward the movable leg 7. As shown in FIG. 2, the rotation-restricting rod 48 normally touches both sides of the second frame 28 to keep the table 25 in an inclined position, thereby preventing said table 25 from rotating in the forward direction A. As used herein, the position in which the table 25 is held by the rotation-restricting rod 48 is referred to as "the normal position of the table 25". When the table 25 is held in the normal position, the stopper pin 21 of the first stopper mechanism 12 is inserted into the engagement hole 24 of the fitting board 4 as shown in FIG. 5. When the table 25 is made to swing in the backward direction opposite to that of the indicated arrow A by the user, the first frame 26 touches the rotation-restricting rod 48 so that the table 25 is inclined in the backward direction from the perpendicular line L (FIG. 14). Thus, the table 25 is prevented by said rotation-restricting rod 48 from being further rotated backward. As used herein, the above-mentioned condition of the table 25 is referred to as "the upside-down position".

Figure 10:
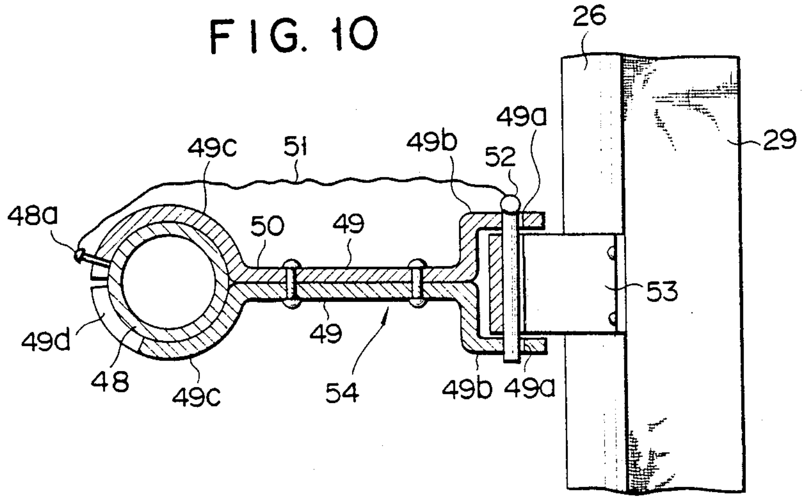
FIG. 10 is a sectional view of the third stopper mechanism.

As shown in FIGS. 9 and 10, a fixing member 50 comprised of a pair of joined plates 49 is rotatably fitted to the intermediate part of the rotation-restricting rod 48. Each of the paired joined plates 49 is provided at one end with an L-shaped bent section 49*b* having a penetrating hole 49*a*, and at the other end with a substantially semicircular curved section 49*c*. The paired semicircular cured sections 49*c* of said fixing member 50 are rotatably fitted to the rotation-restricting rod 48. A groove 49*d* is formed throughout the paired semicircular curved sections 49*c* in a state extending through a total circumferential angle of about 90° around the longitudinal axis of the rod 48. A first pin 48*a* projectively provided on the rotation-restricting rod 48 extends outward through the groove 49*d*. This first pin 48*a* restricts the rotation range of the fixing member 50 within the circumferential angle of 90°. A second pin 52 is connected to the first pin 48*a* by means of a cord 51 as shown in FIG. 10. A pin holder 53 is fixed on the back of the base board 29*a* of the cushion 29 as shown in FIG. 9. After the table 25 is rotated in the backward direction to set a vertical position shown in FIG. 11, the pin holder 53 is inserted into the paired bent sections 49*b* of the fixing member 50 to keep the fixing member 50 in a horizontal position. When, under this condition, the second pin 52 is inserted into the pin holder 53 through the penetrating hole 49*a* of the paired L-shaped bent portions 49*b*, the table 25 is securely set in place by the fixing member 50 in a vertical upside-down position. In other words, the fixing member 50, second pin 52 and pin holder 53 collectively constitute a third stopper mechanism 54.

Figure 12:
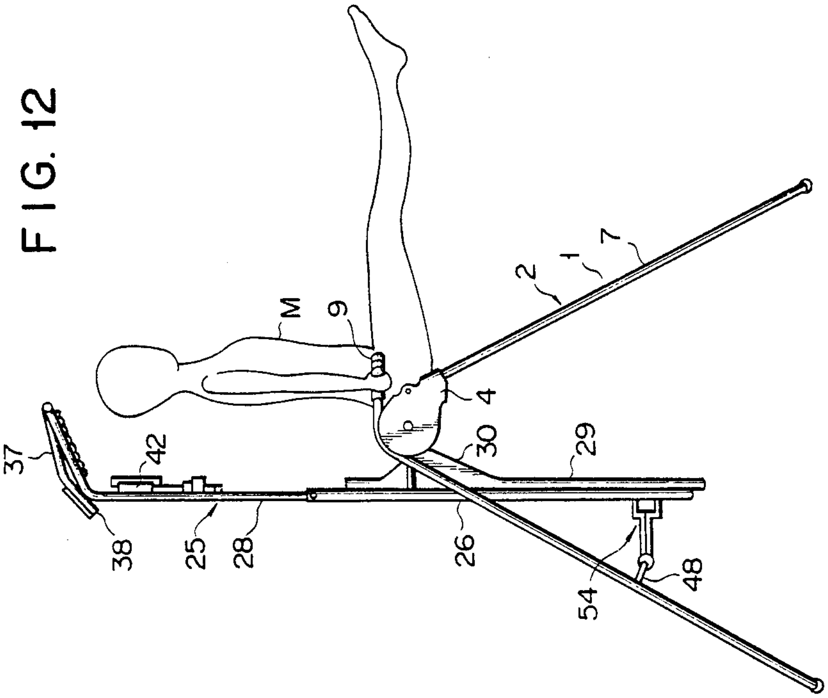
FIGS. 11 to 14 show various ways in which the subject health apparatus can be applied by the user to perform different kinds of physical exercise of the user.
Figure 11:
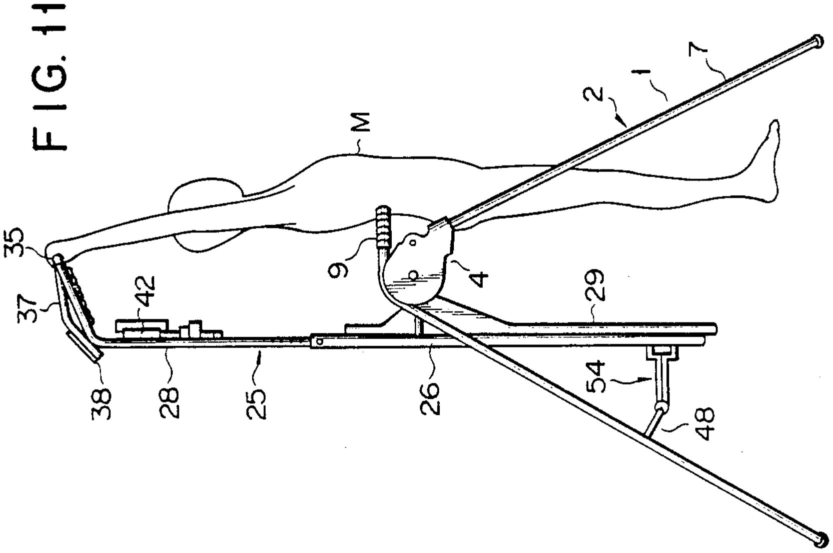

A tilting health table apparatus embodying this invention which is constructed as described above allows the user to perform various physical exercises illustrated in FIGS. 11 to 14. Referring to FIG. 11, the table 25 is rotated in the backward direction, until it is kept in a vertical upside-down position by means of the third stopper mechanism 54. In this condition, the user can perform a hanging exercise by hanging from the paired handles 35. When, as illustrated in FIG. 12, he makes use of the first paired handles 9, the user can perform such exercises as dips, push-ups, or leg-lifts. When the first support board 38 of the support assembly 47 is held on the upper surface of the foot board 31 while the user performs the exercises illustrated in FIGS. 11 and 12, the first support board 38 does not obstruct said exercises.

Figure 13:
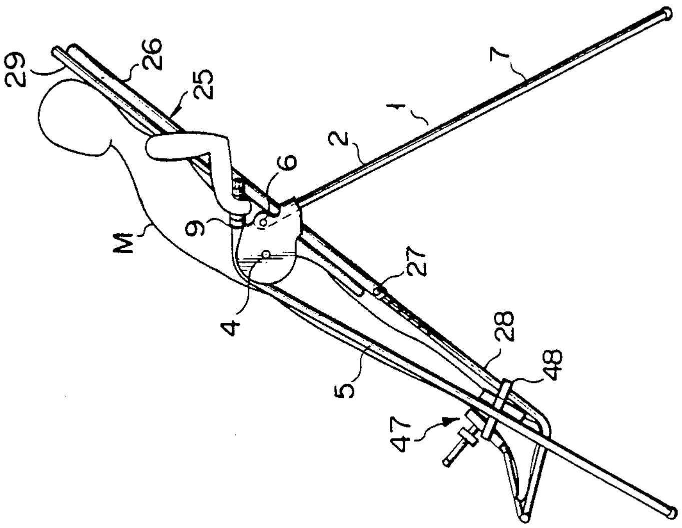

When, as shown in FIG. 13, the foot board 31 is held down to occupy the ordinary position by means of the first stopper mechanism 12 assembled inside of the fitting board 4 and the rotation-restricting rod 48 acting as the second stopper mechanism, the user stands on the mat 33, has his legs securely gripped by the support assembly 47, and leans against the cushion 29. Then the user pulls out the stopper pin 21 of the first stopper mechanism 12 from the engagement hole 24 of the fitting board 4. Further, the user grips the first paired handles 9 with both hands, and pushes the table 25 in the backward direction by himself. As the user rotates the table 25 until it assumes an upside-down position and touches the rotation-restricting rod 48, his head is kept down and his feet are kept up, as illustrated in FIG. 14. Therefore, he can perform a chinning exercise in an inverted position. When the user stands on the mat 33 mounted on the foot board 31, the soles of his feet are pressed by the projections of said mat 33. When the user alternately assumes the ordinary and inverted positions by rotating the table 25, it is possible to improve his blood circulation, activate his metabolism and forestall the sagging of internal organs, such as gastroptosis, for example.

When the table 25 is rotated in the backward direction until it touches the rotation-restricting rod 48 during the chinning exercise in the inverted position indicated in FIG. 14, the rotation of the table 25 is restricted. When, in this condition, the user leans away from the front side of the table 25, while still gripping the first paired handles 9, the shifting of his weight applies a moment to the table 25 to let it rotate in the backward direction. When, therefore, the table 25 touches the rotation-restricting rod 48, the inclined state of said table 25 remains stable, and it becomes difficult to effect forward rotation of the table 25, thereby reliably assuring the inverted chinning exercise.

When the paired movable leg members 7 are drawn toward the paired fixed leg members 5, the whole leg assembly can be flattened for storage. When the second frame 28 of the table 25 is slid toward the first frame 26, and the table 25 is set in a vertical upside-down position, the height of the subject tilting health table apparatus can be reduced and made convenient for storage.

The stopper mechanism used with the tilting health table apparatus of this invention is not limited to that involved in the first embodiment. In said embodiment, the table is fixed by the third stopper mechanism when the hanging exercise is performed with the table kept in an inverted position. However, it is possible to form an engagement hole in the fitting board of the first stopper mechanism instead of the third stopper mechanism, into which the stopper pin can be inserted when the table is set upside down.

Figure 15:
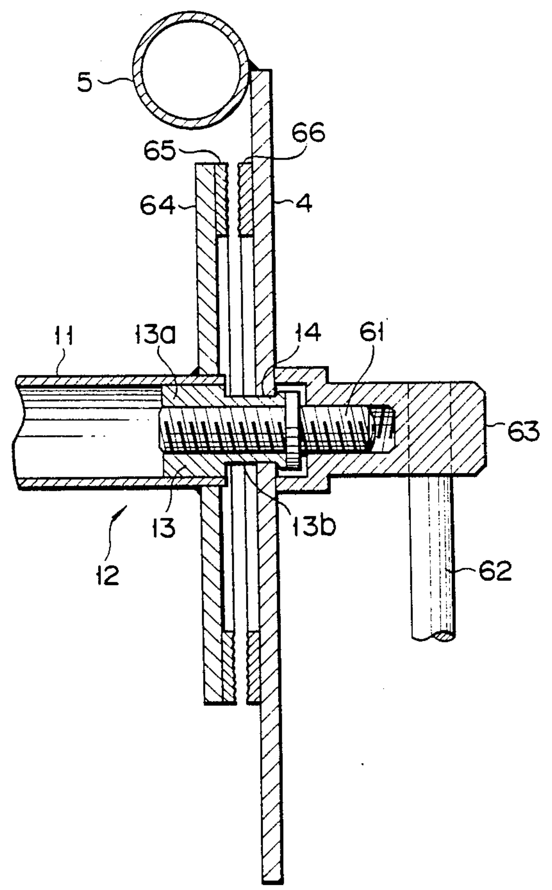
FIG. 15 is a sectional view of a first stopper mechanism involved in a tilting health table apparatus according to a second embodiment of this invention.

Further, the first stopper mechanism may be arranged as shown in FIG. 15. Namely, the larger diameter section 13*a* of a nut 13 is inserted into the end portion of the fitting rod 11. The smaller diameter section 13*b* is rotatably inserted into a support hole 14 bored in the fitting board 4. A screw 61 is threadedly inserted into the nut 13. A cap nut 63 connected to an operation rod 62 is threadedly fitted to that portion of said screw. 61 which projects outward from the fitting board 4. A friction board 64 is fixed to the end of the fitting rod 11 in a state facing the inside of the fitting board 4. A first annular friction member 65 is mounted on the peripheral portion of that side of the friction board 64 which faces the inside of the fitting board 4. A second annular friction member 66 is mounted on the inside of that portion of the fitting board 4 which faces the first friction member 65. Therefore, when the cap nut 63 is tightened by the operation rod 62, the fitting board 4 is pressed by the end face of the cap nut 63 to be elastically deformed. As a result, the second friction member 66 fitted to the fitting board 4 is pressed against the first friction member 65, thereby preventing the rotation of the fitting rod 11.

With the tilting health table apparatus embodying this invention, a pair of first handles are fitted substantially horizontal to both sides of the upper portion of the leg assembly. A table is rotatably mounted on the leg assembly in a state brought to rest at a prescribed rotation angle. A projecting foot board is fitted to the front side of the table. A pair of second handles are projectively fitted to both sides of the foot board. Therefore, the user can perform various physical exercises by making use of the above-mentioned first and second pairs of handles and the table.

What we claim is:

1. A tilting health table apparatus comprising:
- a leg assembly;
- a pair of first handles fitted in a substantially horizontal manner to both sides of the upper portion of the leg assembly;

- a table rotatably mounted on said leg assembly to support a user;
- stopper means for keeping said table in a prescribed position to restrict its movement;
- a foot board mounted on one end of said table, said foot board being provided with a foot-gripping means for securely gripping the user's legs, said foot-gripping means including a first support board rotatably mounted on said table, a second support board fixed to said table and means for securely mounting said first support board on said second support board; and
- a pair of second handles projectively fitted to both sides of said foot board.

2. The tilting health table apparatus according to claim 1, wherein, when said table is rotated in a direction to said the foot board mounted on one end of said table, the further rotation of said table is restricted in a state inclined from the vertical direction.

3. The tilting health table apparatus according to claim 1, wherein said foot board includes a mat mounted thereon, said mat being provided with a large number of projections.

4. The tilting health table apparatus according to claim 1, wherein said table comprises a cushion thereon, said cushion being provided with a protuberance arranged to abut against the user's back.

5. The tilting health table apparatus according to claim 1, wherin said leg assembly includes a fitting board, an immovable leg member fixed at one end to said fitting board, a movable leg member rotatably connected at one end to said fitting board and a stopper section mounted on said fitting board to define the angle through which said movable leg member is separated from said immovable leg member.

6. A tilting health table apparatus comprising:
- a leg assembly;
- a pair of first handles fitted in a substantially horizontal manner to both sides of the upper portion of the leg assembly;
- a table rotatably mounted on said leg assembly to support a user;
- stopper means for keeping said table in a prescribed position to restrict its movement;
- a foot board mounted on one end of said table; and
- a pair of second handles projectively fitted to both sides of said foot board;
- said leg assembly including a fitting board, an immovable leg member fixed at one end to said fitting board, a movable leg member rotatably connected at one end to said fitting board and a stopper section mounted on said fitting board to define the angle through which said movable leg member is separated from said immovable leg member.

7. The tilting health table apparatus according to claim 6, wherein, when said table is rotated in a direction to lift said foot board mounted on one end of said table, the further rotation of said table is restricted in a state inclined from the verical direction.

8. The tilting health table apparatus according to claim 6, wherein said foot board includes a mat mounted thereon, said mat being provided with a large number of projections.

9. The tilting health table apparatus according to claim 6, wherein said foot board is provided with a foot-gripping means for securely gripping the user's legs.

10. The tilting health table apparatus according to claim 6, wherein said table comprises a cushion thereon, said cushion being provided with a protuberance arranged to abut against the user's back.

* * * * *

UNITED STATES PATENT AND TRADEMARK OFFICE

CERTIFICATE OF CORRECTION

PATENT NO. : 4,494,532

DATED : January 22, 1985

INVENTOR(S) : Teruo MASUDA et al

It is certified that error appears in the above-identified patent and that said Letters Patent is hereby corrected as shown below:

COLUMN 6, line 16 (claim 2), change "to said the foot board" to --to lift said foot board--.

Signed and Sealed this

*Twenty-third* Day of *July 1985*

[SEAL]

*Attest:*

DONALD J. QUIGG

*Attesting Officer* *Acting Commissioner of Patents and Trademarks*